(12) United States Patent
Kim

(10) Patent No.: US 7,402,810 B2
(45) Date of Patent: Jul. 22, 2008

(54) X-RAY DETECTING DEVICE AND FABRICATING METHOD THEREOF

(75) Inventor: Ik Soo Kim, Kunpo-shi (KR)

(73) Assignee: LG Display Co., Ltd., Seoul (KR)

( * ) Notice: Subject to any disclaimer, the term of this patent is extended or adjusted under 35 U.S.C. 154(b) by 1680 days.

(21) Appl. No.: 10/025,908

(22) Filed: Dec. 26, 2001

(65) Prior Publication Data
US 2002/0154235 A1    Oct. 24, 2002

(30) Foreign Application Priority Data
Dec. 29, 2000  (KR) .......................... 10-2000-85280

(51) Int. Cl.
*G01T 1/24*  (2006.01)
(52) U.S. Cl. ................................. 250/370.09
(58) Field of Classification Search ............ 250/370.09; 378/98.2; 257/E27.14
See application file for complete search history.

(56) References Cited

U.S. PATENT DOCUMENTS

| | | | |
|---|---|---|---|
| 5,440,130 A * | 8/1995 | Cox et al. | 250/370.09 |
| 5,557,534 A * | 9/1996 | Wu | 716/19 |
| 5,648,674 A * | 7/1997 | Weisfield et al. | 257/428 |
| 6,043,511 A * | 3/2000 | Kim | 257/59 |
| 6,462,344 B1 * | 10/2002 | Joo et al. | 250/370.09 |
| 6,784,434 B2 * | 8/2004 | Hennessy et al. | 250/370.14 |

* cited by examiner

*Primary Examiner*—David P. Porta
*Assistant Examiner*—Marcus H Taningco
(74) *Attorney, Agent, or Firm*—McKenna, Long & Aldridge LLP

(57) ABSTRACT

An X-ray detecting device, and a fabricating method thereof, that reduces ground line breakage. In the device and method, a storage electrode is formed along a ground line. Accordingly, a step between the storage electrode and the ground line is prevented, which reduces ground line breakage.

14 Claims, 11 Drawing Sheets

X-RAY DETECTING DEVICE AND FABRICATING METHOD THEREOF

This application claims the benefit of Korean Patent Application No. P2000-85280, filed on Dec. 29, 2000, which is hereby incorporated by reference.

BACKGROUND OF THE INVENTION

1. Field of the Invention

This invention relates to X-ray detectors. More particularly, it relates to an X-ray detecting device, and to a fabricating method thereof, having reduced ground line breakage.

2. Description of the Related Art

Figure 1:
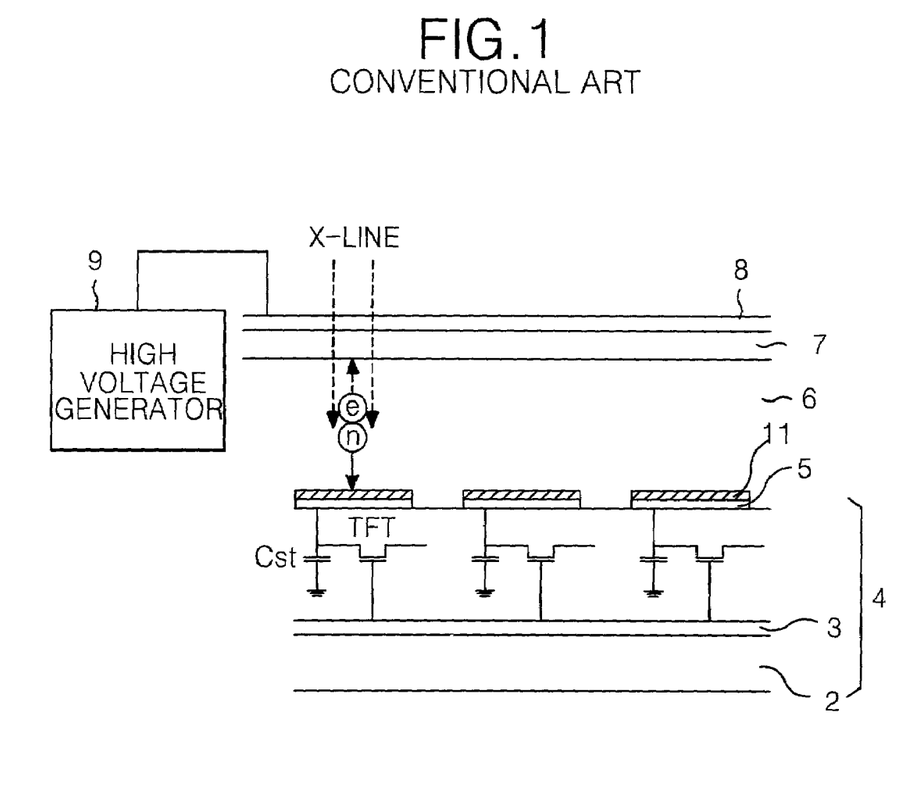
FIG. 1 is a schematic block circuit view showing a panel structure of a conventional X-ray detecting device.

Generally, an X-ray imaging system photographs an object using X-ray sensitive film. Such systems have been useful in medical, scientific, and industrial applications. While photographic films have been useful, another X-ray imaging system that uses X-ray detecting panels to convert X-rays into electrical signals is becoming more common. Such an X-ray detecting panel is illustrated in FIG. 1. That panel includes a photo sensitive layer 6 for converting X-rays into electrical signals and a thin film transistor substrate 4 that selectively outputs those electrical signals.

The thin film transistor substrate 4 includes pixel electrodes 5 that are arranged in a pixel unit and thin film transistors (TFT's). Each thin film transistor is connected to a charging capacitor Cst, to a gate line 3, and to a data line (which is not shown). On the upper portion of the photosensitive layer 6 is a dielectric layer 7 and an upper electrode 8. The upper electrode is connected to a high voltage generator 9. The photosensitive layer 6 is comprised of selenium with a thickness of hundreds of μm. That layer detects incident X-rays and converts them into electrical signals. To do this, the photosensitive layer 6 produces electron-hole pairs in response to incident X-rays. The electron-hole pairs are separated by a high voltage (several kVs) applied to the upper electrode 8 by the high voltage generator 9. Separated charges are stored in the charging capacitor Cst by way of the pixel electrode 5. However, some of the separated charges accumulate on the surface of the pixel electrode 5. This reduces the charge stored in the charging capacitor Cst. In order to prevent such a reduction, a charge-blocking layer 11 is formed on the pixel electrodes 5. The thin film transistors (TFT) respond to gate signals input on the gate line 3 by applying pixel signals from the charging capacitors Cst to data lines. Those pixel signals are applied, via a data reproducer, to a display device that produces an image.

Figure 2:
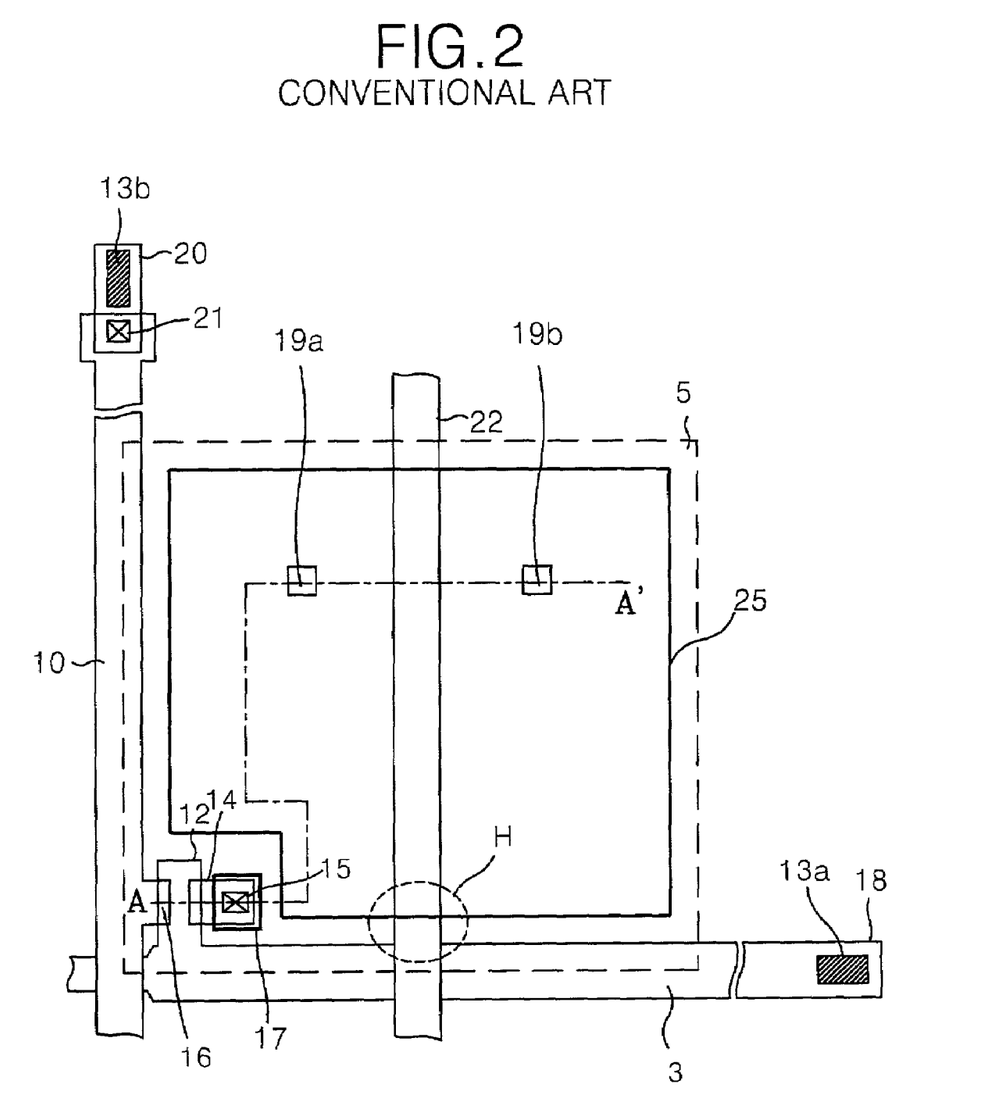
FIG. 2 is a plan view showing a structure of the X-ray detecting device shown in FIG. 1.

FIG. 2 is a plan view showing part of the thin film transistor substrate 4 of FIG. 1. Referring now to FIG. 2, in the thin film transistor substrate 4 each pixel electrode 5 is formed in a unit pixel area defined by gate lines 3 and data lines 10. Each charging capacitor Cst includes a storage electrode 25, a transparent electrode (which is not shown) above the storage electrode 25, and an interposed storage insulation layer 32. A ground line 22 crosses each pixel electrode 5. The ground line resets residual electric charges on the charging capacitor Cst.

Each thin film transistor (TFT) is formed at an intersection between a data line 10 and a gate line 3. Each TFT includes a gate electrode 12 that extends from a gate line 3, a source electrode 16 that extends from a data line 10, a drain electrode 14 that connects, via a drain contact hole 15, to a pixel electrode 5, and semiconductor layers (which are not shown) that connect to the source electrode 16 and to the drain electrode 14.

One end of each gate line 3 and one end of each data line 10 respectively have a gate pad 18 and a data pad 20. Those pads connect to a driving integrated circuit (IC). The gate line 3, the gate electrode 12 and the gate pad 18 are made from the same metallic structure. That structure is beneficially comprised of sequentially disposed aluminum (Al) and molybdenum (Mo). To produce good signal transfer characteristics, the data line 10 is beneficially comprised of a molybdenum metal. The data pad 20 has a structure similar to the gate pad 18. This enables connecting the driving IC using an Al wire bonding. Since the data pads 20 are formed on a level that is different than the data lines 10, the data pads connect to the driving IC(s) via a contact hole 21 that passes through a gate insulating film (which is not shown). The gate pads 18 and the data pads 20 have an Al layer that is exposed, respectively, through contact holes 13a and 13b.

Figure 3A:
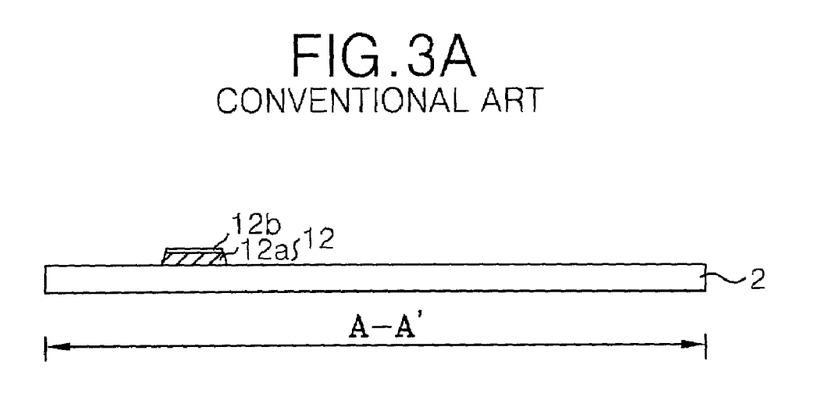
FIG. 3A to FIG. 3G are section views showing a method of fabricating the X-ray detecting device (with the section views taken along line A-A' of FIG. 2)

FIG. 3A to FIG. 3G are section views showing a method of fabricating the thin film transistor substrate shown in FIG. 2. First, as shown in FIG. 3A, the gate electrode 12 is formed by sequentially depositing an Al metal 12a and a Mo metal 12b on a substrate 2, and then patterning those metals.

Figure 3B:
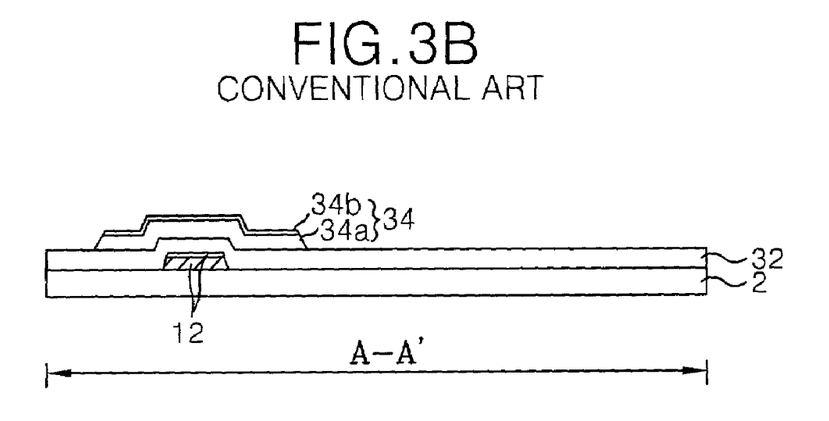

As shown in FIG. 3B, a gate insulating film 32, an active layer 34a, and an ohmic contact layer 34b are then formed by depositing an insulating material and first and second semiconductor layers over the entire surface of the substrate 2 (including over the gate electrode 12), and then patterning the first and second semiconductor layers to form a semiconductor structure 34.

Figure 3C:
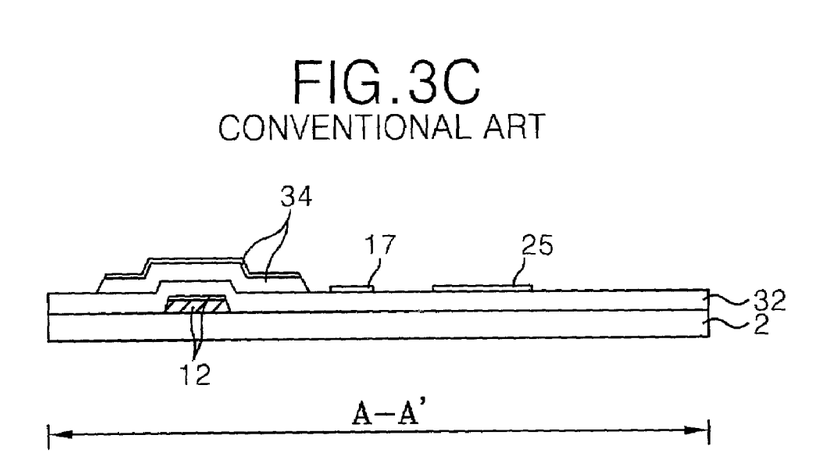
Figure 3D:
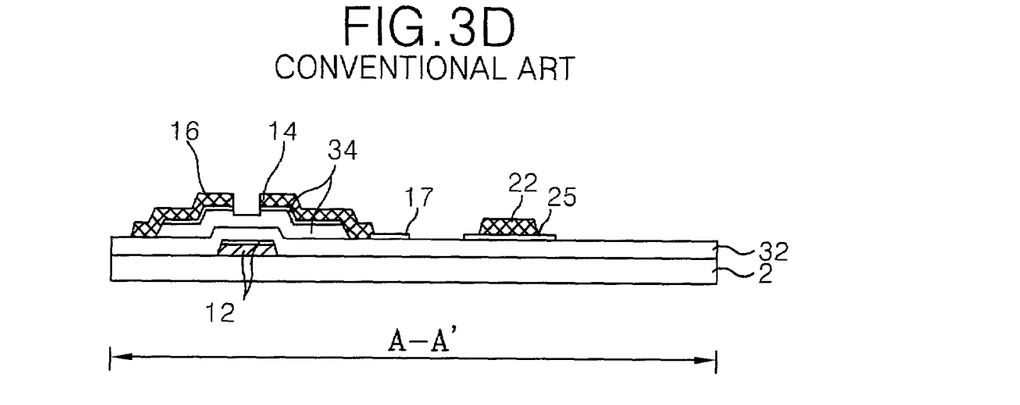

After formation of the semiconductor structure 34, as shown in FIG. 3C, a transparent drain electrode 17 and the storage electrode 25 are formed by depositing and patterning a transparent conductive material over the gate insulating film 32. Then, as shown in FIG. 3D, the source electrode 16, the drain electrode 14, and the ground line 22 are formed by depositing a data metal film over the substrate 2 (including over the transparent drain electrode 17 and over the storage electrode 25) and then patterning the data metal film. The drain electrode 14, the transparent drain electrode 17, and the ground line 22 electrically contact the storage electrode 25. Referring now to FIG. 3F, a storage insulating layer 36 is then formed by depositing an insulating material over the gate insulating film 32 in such a manner as to cover the source electrode 16, the drain electrode 14 and the ground line 22.

Figure 3E:
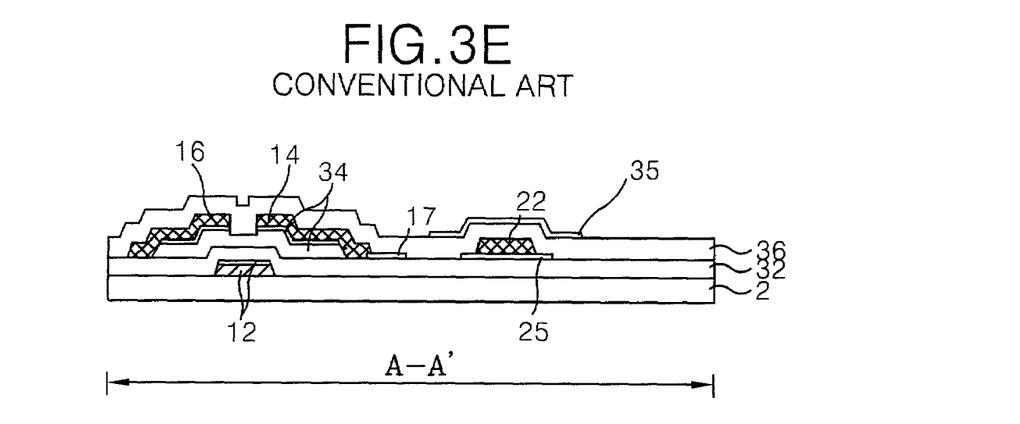
Figure 3F:
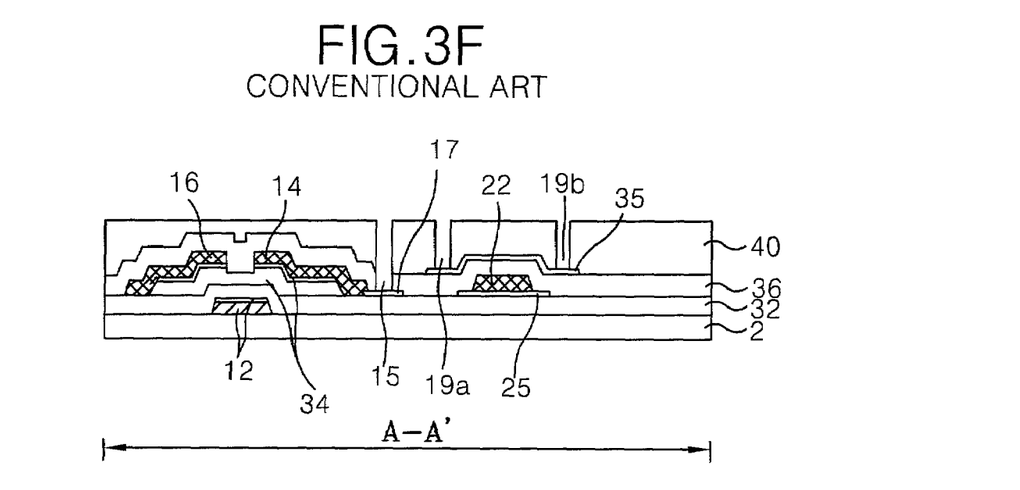

As shown in FIG. 3E, a transparent storage electrode 35 is then formed by depositing a transparent conductive material over the storage insulating layer 36, and then patterning that transparent conductive material. Subsequently, as shown in FIG. 3F, a drain contact hole 15, and first and second storage contact holes 19a and 19b are formed by depositing an insulating material over the storage insulating layer 36 to form a protective layer 40, and then patterning that protective layer 40 to form the holes.

Figure 3G:
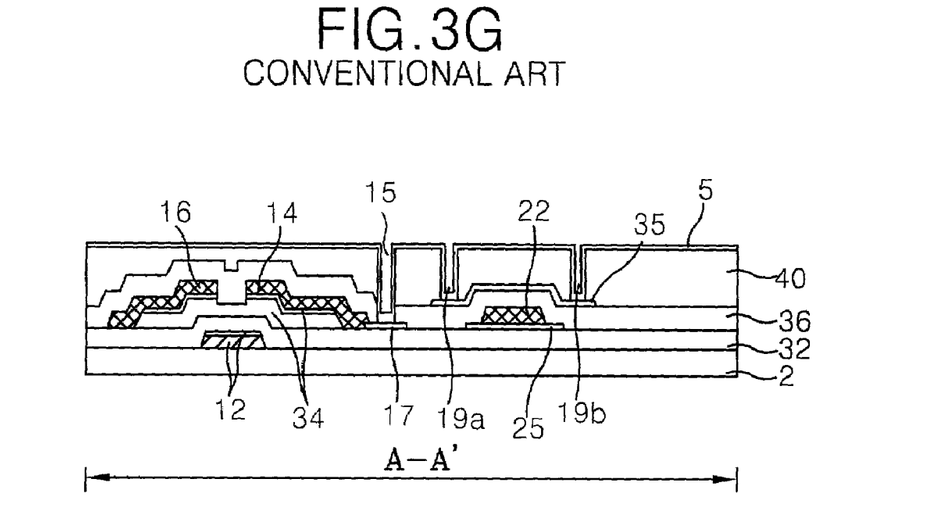

Finally, as shown in FIG. 3G, a pixel electrode 5 that is electrically connected to the transparent drain electrode 17 and to the transparent storage electrode 35 is then formed by depositing a transparent conductive material onto the protective film 40, and then patterning that transparent conductive material.

Figure 4:
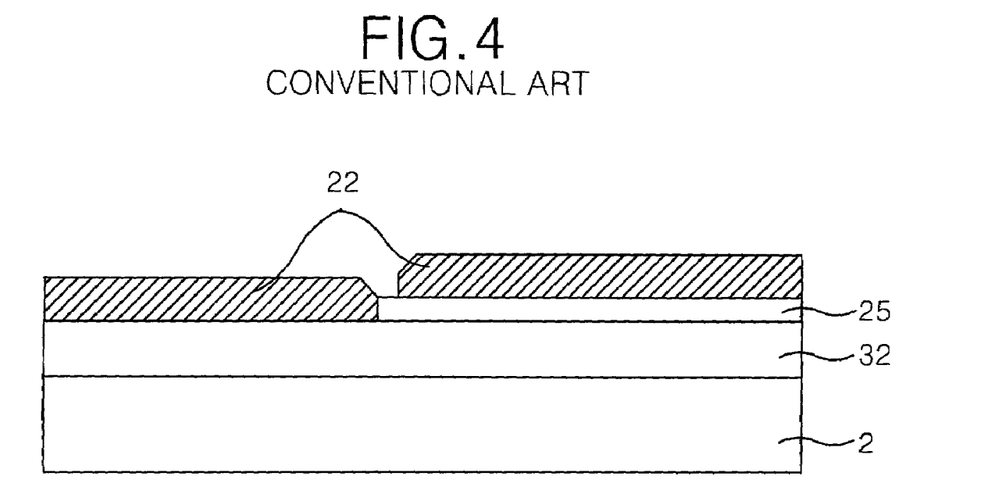
FIG. 4 is a section view of area "H" of FIG. 2.

Referring now to FIG. 2, the storage electrode 25 and the gate line 3 are spaced at a desired distance H. Thus, the storage electrode 25 is formed on the gate insulating film 32 (see FIG. 3C) in such a manner as to produce a step as shown in FIG. 4. If a ground line 22 is formed on the storage electrode 25 over the step breaking the ground line 22 at the step can occur.

SUMMARY OF THE INVENTION

Accordingly, it is an object of the present invention to provide an X-ray detecting device, and a fabricating method thereof, that is capable of reducing ground line breakage.

In order to achieve that and other objects of the invention, an X-ray detecting device according to one aspect of the present invention includes a ground line connected to each X-ray detecting cell in a column. A storage electrode extends into each X-ray detecting cell and connects to the ground line. Additionally, a pixel electrode is provided at each X-ray detecting cell.

The X-ray detecting device further includes a plurality of thin film transistors, each having a gate electrode connected to a gate line; a source electrode connected to a data line; and a drain electrode connected to a pixel electrode.

The X-ray detecting device further includes a gate insulating film that insulates the gate electrodes, the source electrodes and the drain electrodes; a storage insulating layer that covers the source electrodes and the drain electrodes; a protective film on the storage insulating layer; and drain contact holes that enable pixel electrodes and drain electrodes on the protective film to be in electrical contact.

The X-ray detecting device further includes an overlapping transparent storage electrode, with the storage electrode having the storage insulating layer therebetween; and a storage contact hole for allowing pixel electrodes and the transparent storage electrode to be connected to the protective film.

In the X-ray detecting device, the transparent storage electrode is formed from a transparent conductive material, which is beneficially selected from any one of indium-tin-oxide (ITO), indium-zinc-oxide (IZO) and indium-tin-zinc-oxide (ITZO).

The ground line is beneficially formed from any one of chrome (Cr) or molybdenum (Mo).

The X-ray detecting device beneficially further includes an auxiliary data line formed along each of the data lines. That auxiliary data line is beneficially formed from a transparent conductive material selected from indium-tin-oxide (ITO), indium-zinc-oxide (IZO) and indium-tin-zinc-oxide (ITZO).

The direction of the column is beneficially parallel with the data lines.

A method of fabricating an X-ray detecting device according to another aspect of the present invention includes forming a gate insulating layer on a substrate that covers a plurality of gate lines; forming a storage electrode for each X-ray detecting cell on the gate insulating layer, with the storage electrodes being interconnected in a column direction; forming a ground line that is connected to the storage electrodes so as to apply a ground voltage to each of the X-ray detecting cells; coating a storage insulating film on the gate insulating film; preventing etching of the storage insulating layer; forming a protective film on the storage insulating film; defining a contact hole in the protective film; and forming a pixel electrode connected, via the contact hole, to the electrode on the protective film.

The method further includes the steps of forming gate electrodes, each connected to a gate line; forming source electrodes, each connected to a data lines, and forming drain electrodes, each connected to a pixel electrode.

In the method, the storage electrode is beneficially formed from a transparent conductive material, which is selected from indium-tin-oxide (ITO), indium-zinc-oxide (IZO) and indium-tin-zinc-oxide (ITZO).

The ground line is beneficially formed from chrome (Cr) or molybdenum (Mo).

The method further includes the step of forming an auxiliary data line along each of the data lines. In the method, the auxiliary data line is beneficially formed from a transparent conductive material, which is selected from indium-tin-oxide (ITO), indium-zinc-oxide (IZO) and indium-tin-zinc-oxide (ITZO).

BRIEF DESCRIPTION OF THE DRAWINGS

These and other objects of the invention will be apparent from the following detailed description of the embodiments of the present invention with reference to the accompanying drawings, in which.

DETAILED DESCRIPTION OF THE ILLUSTRATED EMBODIMENTS

Figure 5:
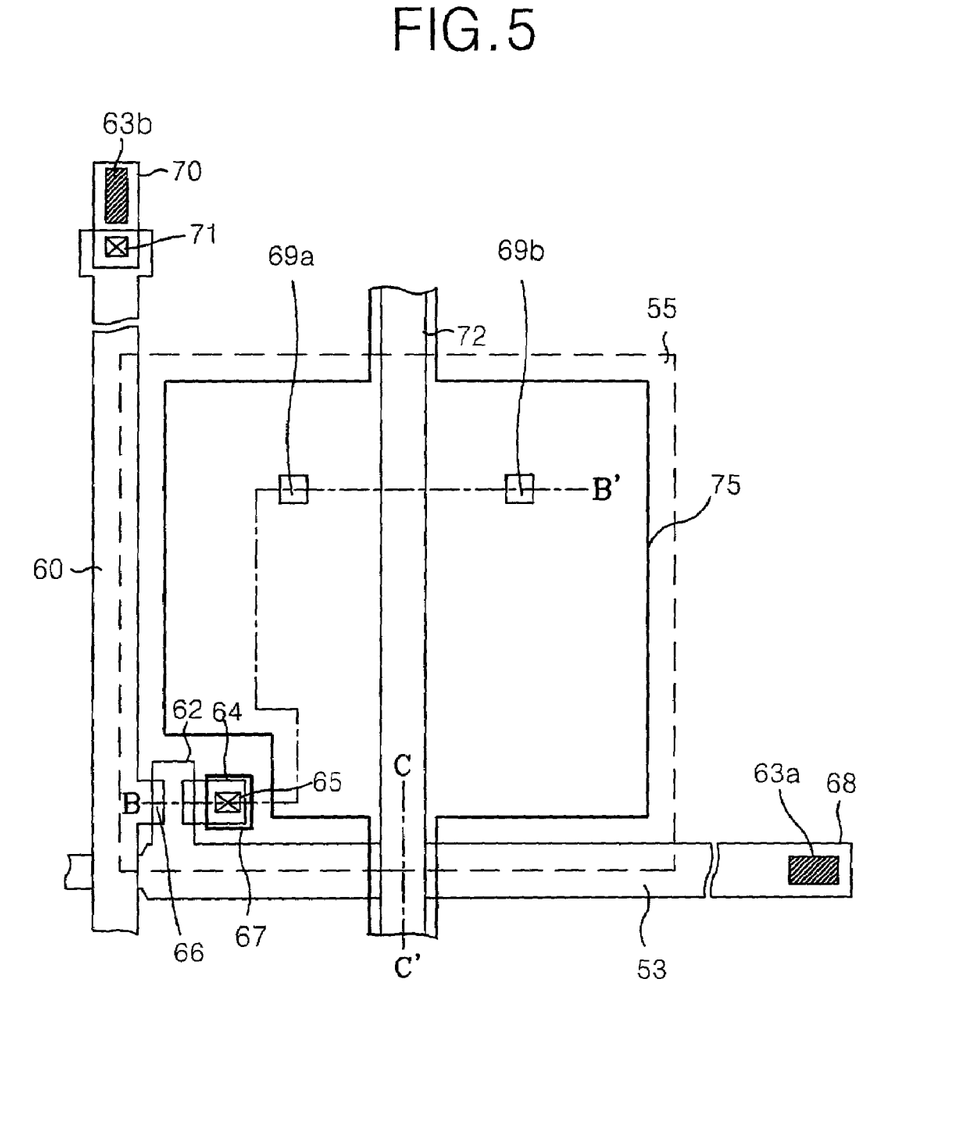
FIG. 5 is a plan view showing a structure of an X-ray detecting device according to a first embodiment of the present invention.

Referring now to FIG. 5, there is shown an X-ray detecting device according to a first embodiment of the present invention. As shown, a pixel electrode 55 is formed in a pixel area partially defined by a gate line 53 and a data line 60 (in practice there are a plurality of gate lines and data lines that are arranged in a matrix). A charging capacitor Cst is formed from a storage electrode 75, a transparent electrode (which is not shown in FIG. 5, but which is discussed in more detail subsequently) adjacent the storage electrode 75, and an interposed storage insulation layer (which also is not shown in FIG. 5, but which is discussed in more detail subsequently). In contrast to the storage electrode 25 shown in FIG. 2, the storage electrode 75 extends along a ground line 72 and over the gate line 53. Accordingly, breakage of the ground line 72 caused by a step (reference FIG. 4) is reduced. Further, the storage electrode 75 extends into adjacent pixels. The ground line 72 crossing the pixel electrode 55 and is used to reset residual electric charges on the charging capacitor Cst.

Still referring to FIG. 5, a thin film transistor (TFT) is formed at an intersection between the data line 60 and the gate line 53. That TFT includes a gate electrode 62 that extends from the gate line 53, a source electrode 66 that extends from the data line 60, a drain electrode 64 that connects to the pixel electrode 55, and semiconductor layers (which are not shown in FIG. 5) that connect to the source electrode 66 and to the drain electrode 64.

An end of the gate line 53 and an end of the data line 60 are provided with, respectively, a gate pad 68 and a data pad 70. Those pads connect to a driving integrated circuit (IC). The gate line 53, the gate electrode 62, and the gate pad 68 are beneficially made from the same metal material, which can be an aluminum (Al) and molybdenum (Mo) structure. The data line 60 is beneficially made from a molybdenum metal (which produces good signal transfer characteristics). The data pad 70 beneficially has a structure like the gate pad 68, which enables making a connection to the driving IC using an Al wire bonding. Thus, since the data pad 70 is formed on a different layer than the data line 60, the date pad is connected to the driving IC via a contact hole 71 passing through a gate insulating film (which is not shown in FIG. 5). The gate pad 68 and the data pad 70 have an Al layer exposed through respective contact holes 63a and 63b that are used to connect the driving IC.

Figure 6A:
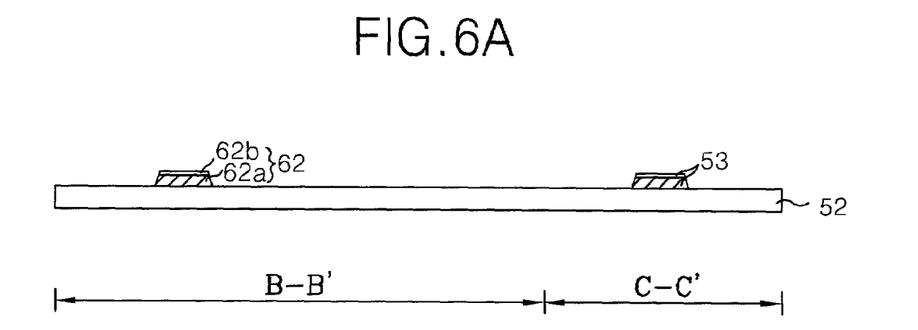
FIG. 6A to FIG. 6G are section views showing a method of fabricating the X-ray detecting device (with the section views taken along lines B-B' and C-C' of FIG. 5)
Figure 6B:
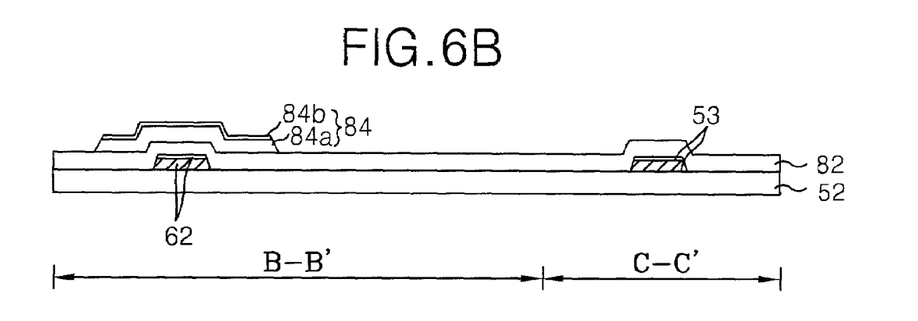

FIG. 6A to FIG. 6G are section views showing a method of fabricating the structures shown in FIG. 5. Those section views emphasize a thin film transistor part and a storage capacitor part. Referring first to FIG. 6A, the gate line 53 and the gate electrode 62 are provided on the substrate 52. The gate line 53 and the gate electrode 62 are beneficially formed by sequentially depositing an Al layer 62a and a Mo layer 62b using a deposition technique (such as a sputtering) and then patterning those layers.

Referring now to FIG. 6, an active layer 84a and an ohmic contact layer 84b are then provided on a gate insulating film 82. The gate insulating film 82 is formed by depositing an insulating material over the substrate 52 (such as by using a plasma enhanced chemical vapor deposition (PECVD) technique) so as to cover the gate line 53 and the gate electrode 62. The gate insulating film 82 is beneficially made from an insulating material such as silicon nitride ($SiN_x$) or silicon oxide ($SiO_x$), etc. Then, the active layer 84a and the ohmic contact layer 84b are formed by disposing first and second semiconductor materials on the gate insulating film 82. Those layers are then patterned. The active layer 84a is made from intrinsic amorphous silicon, while the ohmic contact layer 84b is made from doped amorphous silicon.

Figure 6C:
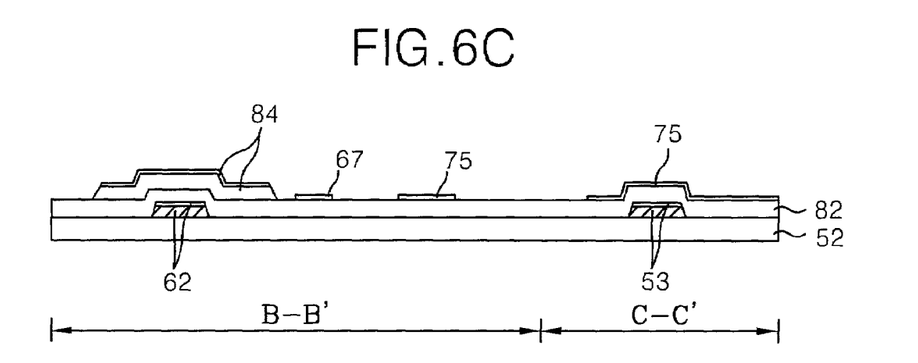

Referring now to FIG. 6C, a transparent drain electrode 67 and the storage electrode 75 are then provided on the gate insulating film 82. The transparent drain electrode 67 and the storage electrode 75 are formed by depositing a transparent conductive material on the gate insulating film 82, and then by patterning that transparent conductive material. The storage electrode 75 is formed so as to extend along a ground line that is formed subsequently. While FIG. 5 shows only one full pixel area, it should be understood that the illustrated full pixel area is replicated in a matrix fashion. Further, as shown in FIG. 5, the storage electrode 75 extends into the other pixel areas. Thus, the storage electrodes of each pixel area are connected to each other. The transparent drain electrode 67 and the storage electrode 75 are beneficially formed from indium-tin-oxide (ITO), indium-zinc-oxide (IZO) and/or indium-tin-zinc-oxide (ITZO).

Figure 6D:
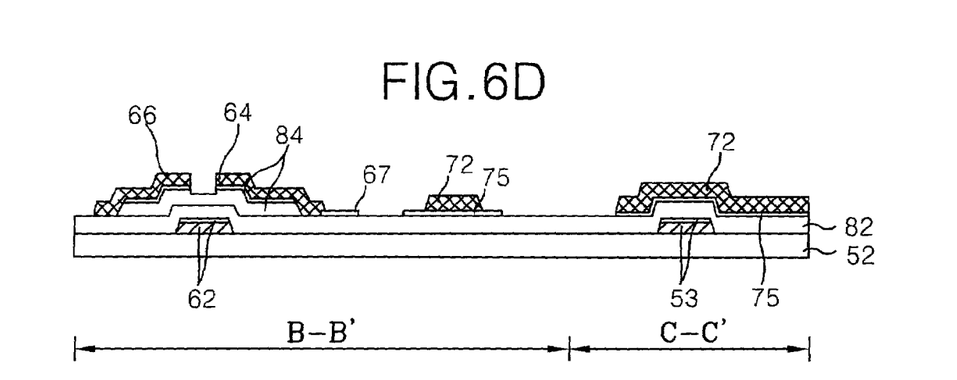

Referring now to FIG. 6D, the source electrode 66, the drain electrode 64 and the ground line 72 are then provided on the gate insulating film 82. The ground line 72 and the source and drain electrodes 66 and 64 are formed by depositing a metal material (such as by using CVD or sputtering) and then by patterning that metal material. After the source and drain electrodes 66 and 64 are patterned, the ohmic contact layer 84b over the gate electrode 62 is patterned to expose the active layer 84a (see FIG. 6B). The active layer 84a between the source and drain electrodes 66 and 64 forms a channel. The ground line 72 is formed along the storage electrode 75 so as to cross the gate line 53 and a pixel electrode that is formed subsequently. The ground line 72 and the source and drain electrodes 66 and 64 are beneficially formed from chrome (Cr) or molybdenum (Mo), etc.

Figure 6E:
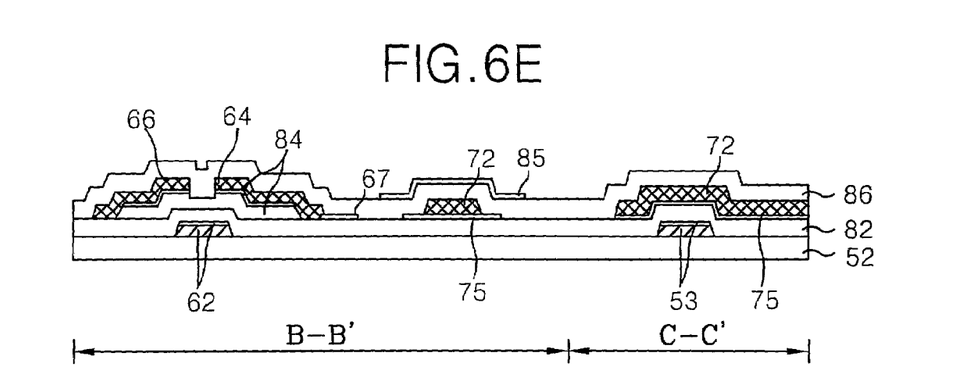

Referring now to FIG. 6E, a transparent storage electrode 85 is provided on a storage insulating layer 86. The storage insulating layer 86 is formed by depositing an insulating material in such a manner as to cover the source electrode 66, the drain electrode 64 and the ground line 72. The transparent storage electrode 85 is beneficially formed by depositing the same material used to make the transparent drain electrode 67 onto the storage insulating layer 86, and then patterning the transparent material for form. The transparent storage electrode 85 will act as an etching stopper in a later step.

A storage capacitor is formed by the transparent storage electrode 85, the storage electrode 75, and the storage insulating layer 86. The storage insulating layer 86 is beneficially made from an inorganic insulating material such as silicon nitride ($SiN_x$) or silicon oxide ($SiO_x$). The transparent storage electrode 85 is beneficially made from a transparent conductive material such as ITO, IZO or ITZO.

Figure 6F:
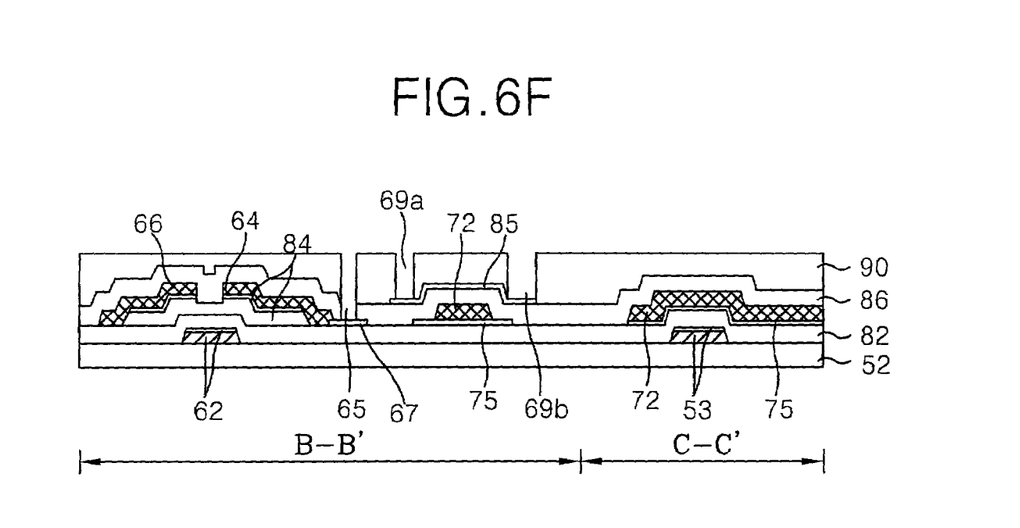

Referring now to FIG. 6F, a protective layer 90 is then provided on the storage insulating layer 86. The protective layer 90 is formed by depositing an insulating material onto the storage insulating layer 86 in such a manner as to cover the transparent storage electrode 85, and then by patterning that insulating material. Additionally, first and second storage contact holes 69a and 69b that pass through the protective layer 90 are defined so as to partially expose the transparent storage electrode 85. Further, a drain contact hole 65 that passes through the storage insulating layer 86 and the protective layer 90 and that exposes the transparent drain electrode 67 is also defined. The protective layer 90 is beneficially comprised of an organic insulating material such as an acrylic organic compound, Teflon, BCB (benzocyclobutene), Cytop or PFCB (perfluorocyclobutane), etc.

Figure 6G:
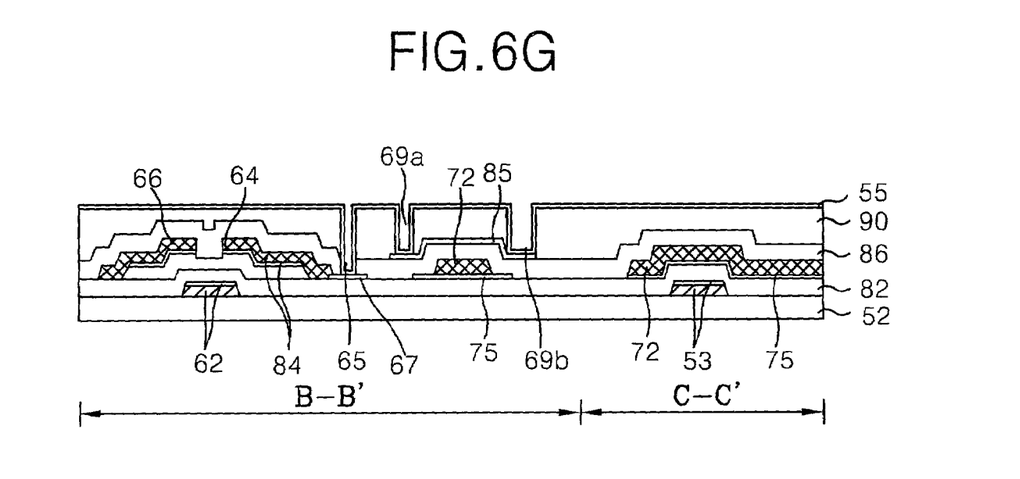

Referring now to FIG. 6G, the pixel electrode 55 is then provided on the protective layer 90. The pixel electrode 55 is formed by depositing a transparent conductive material over the protective layer 90, and then by patterning that transparent conductive material. The pixel electrode 55 electrically contacts the drain electrode 64 through the transparent drain electrode 67 that is exposed via the drain contact hole 65. The pixel electrode also electrically contacts the transparent storage electrode 85 via the first and second storage contact holes 69a and 69b. The pixel electrode 55 is beneficially comprised of indium-tin-oxide (ITO), indium-zinc-oxide (IZO) and/or indium-tin-zinc-oxide (ITZO).

Figure 7:
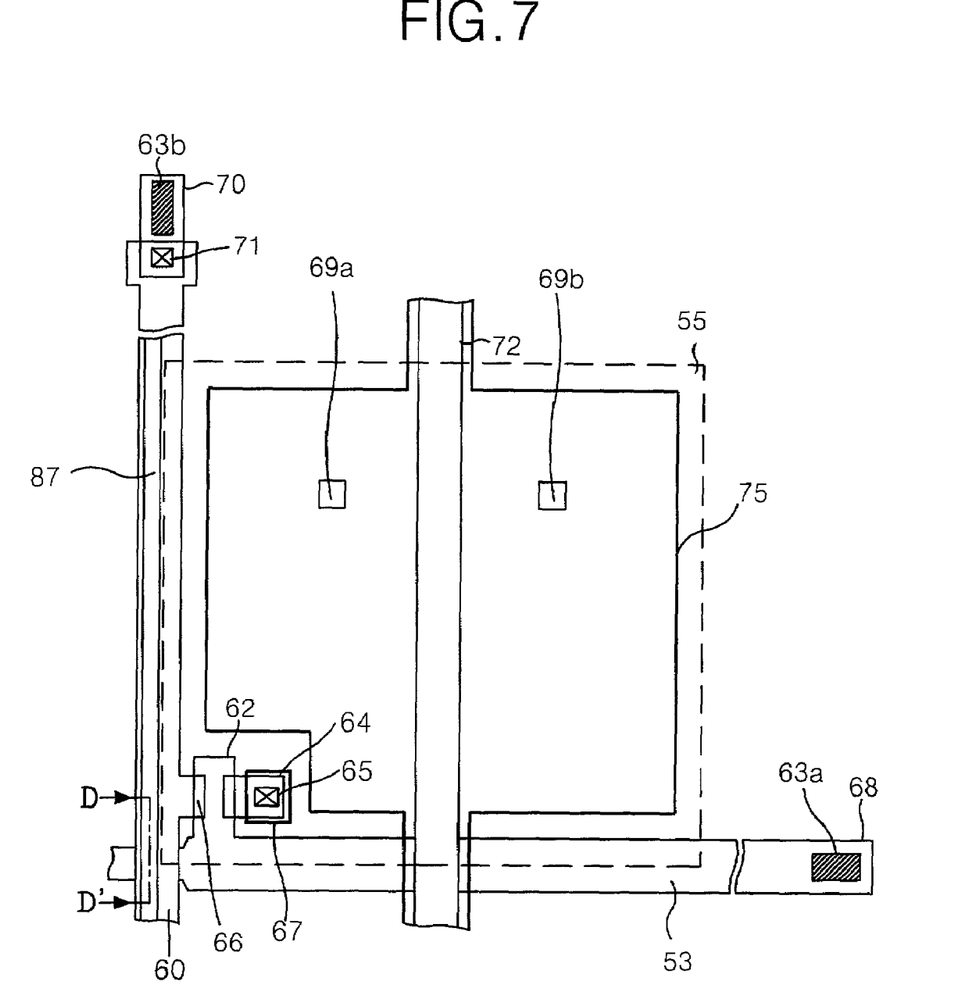
FIG. 7 is a plan view showing a structure of an X-ray detecting device according to a second embodiment of the present invention.
Figure 8:
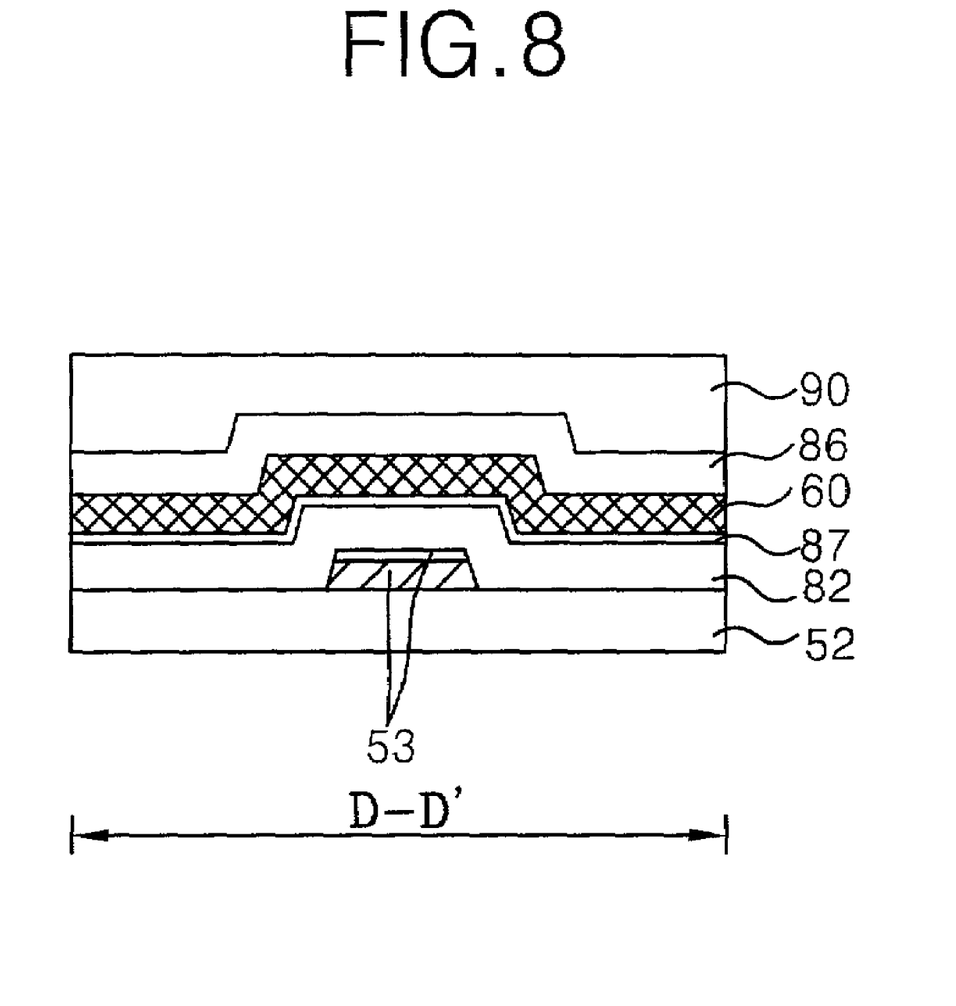
FIG. 8 is a section view along line D-D' of FIG. 7.

FIG. 7 and FIG. 8 show an X-ray detecting device according to a second embodiment of the present invention. That X-ray detecting device includes elements similar to the X-ray detecting device shown in FIG. 5, except that an auxiliary transparent line 87 is provided on the data line 60.

The auxiliary transparent line 87 is formed along and on the data line 60. Accordingly, it becomes possible to prevent step-induced problems where the gate line 53 crosses the data line 60, as well as breakage of the data line 60 caused by particles created during deposition. Furthermore, it becomes possible to reduce the resistance of the data line 60.

Hereinafter, a method of fabricating a data line part of such an X-ray detecting device will be described. Referring now to FIG. 8, first, the gate line 53 is formed by depositing and patterning a metal layer on the substrate 52. The gate insulating film 82 is then formed over the substrate 52 and the gate line 53. Then, an auxiliary transparent line 87 is formed by depositing and patterning a transparent conductive material. The data line 60 is then formed by depositing a metal layer over the auxiliary transparent line 87 and then by patterning that metal layer. Subsequently, a storage insulating layer 86 and a protective layer 90 are sequentially formed so as to cover the data line 60. The pixel electrode 55 (not shown in FIG. 8, but reference FIG. 7) is then formed by depositing and patterning a transparent conductive material on the protective layer 90.

As described above, according to the present invention, a storage electrode is formed along the ground line. Accordingly, a step between the storage electrode and the ground line can be eliminated, reducing or preventing breakage of the ground line. Further, the storage electrodes of the pixels are connected to each other, thereby reducing the resistance of the ground line. Moreover, an auxiliary transparent line can be formed along the data line on the data line, so that it becomes possible to prevent a breakage of the data line as well as to reduce a resistance of the data line.

Although the present invention has been explained by the embodiments shown in the drawings described above, it should be understood that the invention is not limited to those embodiments, but rather that various changes or modifications thereof are possible without departing from the spirit of the invention. Accordingly, the scope of the invention shall be determined according to the appended claims and their equivalents.

What is claimed is:

1. An X-ray detecting device having X-ray detecting cells arranged at intersections between data lines and gate lines, said device comprising: a ground line that extends along a column direction, said ground line connected to a plurality of X-ray detecting cells so as to apply a ground voltage; a storage electrode connected to said ground line, said storage electrode electrically connected to said plurality of X-ray detecting cells; and a pixel electrode in each X-ray detecting cell of said plurality of X-ray detecting cells whererin said storage eletrodes of adjacent X-ray detecting cells along said column direction are connection to each other.

2. The X-ray detecting device according to claim 1, further comprising:
   a thin film transistor having a gate electrode connected to a gate line; a source electrode connected to a data line; and a drain electrode connected to a pixel electrode.

3. The X-ray detecting device according to claim 2, further comprising:
   a gate insulating film insulating said gate electrode, said source electrode, and said drain electrode;
   a storage-insulating layer covering said source electrode and said drain electrode;
   a protective film on said storage insulating layer; and
   a drain contact hole for allowing said pixel electrode and said drain electrode to be in electrical contact with each other.

4. The X-ray detecting device according to claim 3, further comprising:
   a transparent storage electrode overlapping said storage electrode, wherein said storage insulating layer is interposed therebetween; and
   a storage contact hole for allowing said pixel electrode and said transparent storage electrode to be connected through said protective film.

5. The X-ray detecting device according to claim 4, wherein said transparent storage electrode is formed from a transparent conductive material that is selected from a group consisting of indium-tin-oxide (ITO), indium-zinc-oxide (IZO), and indium-tin-zinc-oxide (ITZO).

6. The X-ray detecting device according to claim 4, wherein said ground line is formed from a group consisting of chrome (Cr) and molybdenum (Mo).

7. The X-ray detecting device according to claim 4, wherein said auxiliary data line is formed from a transparent conductive material that is selected from indium-tin-oxide (ITO), indium-zinc-oxide (IZO) and indium-tin-zinc-oxide (ITZO).

8. The X-ray detecting device according to claim 1, further comprising an auxiliary data line formed along each of said data lines.

9. A method of fabricating an X-ray detecting device having X-ray detecting cells arranged at intersections between data lines and gate lines, the method comprising the steps of:
   forming a gate-insulating layer on a substrate and over the gate lines;
   forming a storage electrode connected to adjacent X-ray detecting cells along a column direction parallel to said data line;
   forming a ground line connected to the storage electrode so as to apply a ground voltage to the adjacent X-ray detecting cells;
   coating a storage insulating film on the gate insulating film;
   forming a storage electrode for preventing etching of the storage-insulating layer;
   forming a protective film on the storage insulating film;
   defining a contact hole in the protective film; and
   forming a pixel electrode connected, via the contact hole, to an electrode on the protective film,
   wherein said storage eletrodes of said adjacent X-ray detecting cells along said column direction are connected to each other.

10. The method according to claim 9, further comprising the steps of:
    forming a gate electrode connected to a gate line;
    forming a source electrode connected to a data line and a drain electrode connected to a pixel electrode on the gate insulating film; and
    forming a drain electrode connected to the pixel electrode.

11. The method according to claim 9, wherein the storage electrode is formed from a transparent conductive material that is selected from indium-tin-oxide (ITO), indium-zinc-oxide (IZO) and indium-tin-zinc-oxide (ITZO).

12. The method according to claim 9, wherein the ground line is formed from chrome (Cr) or molybdenum (Mo).

13. The method according to claim 9, further comprising the step of forming an auxiliary data line along a data line.

14. The method according to claim 13, wherein the auxiliary data line is formed from a transparent conductive material that is selected from a group consisting of indium-tin-oxide (ITO), indium-zinc-oxide (IZO) and indium-tin-zinc-oxide (ITZO).

* * * * *